US012635959B1

(12) United States Patent
Mehta et al.

(10) Patent No.: US 12,635,959 B1
(45) Date of Patent: May 26, 2026

(54) PATIENT-TRIGGERED SYSTEM FOR CARDIAC EMERGENCIES

(71) Applicants: Sameer Mehta, New York, NY (US); Annapoorna Kini, New York, NY (US); Samin K. Sharma, New York, NY (US)

(72) Inventors: Sameer Mehta, New York, NY (US); Annapoorna Kini, New York, NY (US); Samin K. Sharma, New York, NY (US)

( * ) Notice: Subject to any disclaimer, the term of this patent is extended or adjusted under 35 U.S.C. 154(b) by 471 days.

(21) Appl. No.: 18/127,477

(22) Filed: Mar. 28, 2023

Related U.S. Application Data

(60) Provisional application No. 63/324,446, filed on Mar. 28, 2022.

(51) Int. Cl.
*A61B 5/00* (2006.01)
*A61B 5/318* (2021.01)

(52) U.S. Cl.
CPC .............. *A61B 5/746* (2013.01); *A61B 5/318* (2021.01)

(58) Field of Classification Search
CPC ........ A61B 5/746; A61B 5/318; G16H 50/20; G16H 50/30; G16H 40/63; G16H 40/67; G16H 20/10; G16H 20/40; G16H 10/60; G16H 10/20; G16H 15/00; G16H 40/20; G16H 20/00; G16H 80/00; G16H 20/30; G16H 50/70; G16H 70/40; G16H 20/70; G16H 70/20; G16H 40/40; G16H 40/60; G16H 10/00; G16H 10/65; G16H 20/13; G16H 20/60; G16H 30/00; G16H 30/20; G16H 40/00; H04W 40/00; H04W 76/10; H04W 8/22; H04W 84/12; H04W 4/00; H04W 4/70; H04W 4/90; H04W 40/02; H04W 84/18
See application file for complete search history.

(56) References Cited

U.S. PATENT DOCUMENTS

| | | | |
|---|---|---|---|
| 5,050,612 A | 9/1991 | Matsumura | |
| 8,923,957 B2 | 12/2014 | Yuk | |
| 9,693,711 B2 | 7/2017 | Yuen et al. | |
| 9,918,664 B2 | 3/2018 | Blahnik et al. | |
| 9,999,744 B2 | 6/2018 | Proud | |
| 10,272,294 B2 | 4/2019 | Williams et al. | |
| 10,503,268 B2 | 12/2019 | Yuen et al. | |
| 11,207,031 B2 | 12/2021 | Mehta et al. | |
| 2001/0051765 A1 * | 12/2001 | Walker .................. | G16H 80/00 600/300 |

(Continued)

OTHER PUBLICATIONS

Sameer Mehta, Final Office Action issued in related U.S. Appl. No. 16/654,979, filed May 7, 2020.

(Continued)

*Primary Examiner* — Ryan W Sherwin
(74) *Attorney, Agent, or Firm* — MALLOY & MALLOY, PL

(57) ABSTRACT

A patient-triggered system for cardiac emergencies, comprising a multi-alert signal configured to bypass at least one bottleneck department, a central processor configured to transmit the multi-alert signal, a patient assembly configured to communicate with the central processor, an emergency services assembly, a hospital assembly, and a highest authority assembly configured to communicate with the hospital assembly and the emergency services assembly.

21 Claims, 2 Drawing Sheets

100

(56)                References Cited

U.S. PATENT DOCUMENTS

| | | | | |
|---|---|---|---|---|
| 2003/0233129 | A1* | 12/2003 | Matos ................. | A61N 1/0476 |
| | | | | 607/5 |
| 2005/0015115 | A1 | 1/2005 | Sullivan et al. | |
| 2005/0085736 | A1 | 4/2005 | Ambrose et al. | |
| 2005/0278195 | A1 | 12/2005 | Getz | |
| 2007/0035403 | A1* | 2/2007 | Krishna ............... | G08B 25/016 |
| | | | | 340/573.1 |
| 2007/0173887 | A1 | 7/2007 | Sasaki | |
| 2009/0247835 | A1* | 10/2009 | Voipio .................. | A61B 5/308 |
| | | | | 600/509 |
| 2009/0281441 | A1 | 11/2009 | Zhang et al. | |
| 2010/0113950 | A1 | 5/2010 | Lin et al. | |
| 2012/0108917 | A1* | 5/2012 | Libbus .................. | A61B 5/002 |
| | | | | 705/2 |
| 2013/0024382 | A1* | 1/2013 | Dala ................... | H04L 63/0464 |
| | | | | 705/51 |
| 2013/0054265 | A1* | 2/2013 | Warner ................. | G16H 40/20 |
| | | | | 705/3 |
| 2015/0005650 | A1 | 1/2015 | Banet et al. | |
| 2015/0018660 | A1 | 1/2015 | Thomson et al. | |
| 2015/0257647 | A1 | 9/2015 | Buck et al. | |
| 2015/0366518 | A1 | 12/2015 | Sampson | |
| 2016/0045167 | A1 | 2/2016 | Gheeraert et al. | |
| 2016/0135706 | A1 | 5/2016 | Sullivan et al. | |
| 2017/0281277 | A1 | 10/2017 | Gregg et al. | |
| 2018/0296105 | A1 | 10/2018 | Blake et al. | |
| 2018/0333063 | A1 | 11/2018 | Muchhala et al. | |
| 2019/0272920 | A1 | 9/2019 | Teplitzky | |
| 2019/0336020 | A1 | 11/2019 | Kranz | |
| 2020/0100693 | A1 | 4/2020 | Velo | |
| 2021/0057112 | A1* | 2/2021 | Mansi ................. | G06F 16/9017 |
| 2022/0262078 | A1* | 8/2022 | Aslam .................. | G06T 19/006 |

OTHER PUBLICATIONS

Sameer Mehta, Final Office Action issued in related U.S. Appl. No. 16/654,970, filed Nov. 30, 2020.

Sameer Mehta, Final Office Action issued in related U.S. Appl. No. 16/654,854, filed Oct. 4, 2021.

Mathews et al., A novel application of deep learning for single-lead ECG classification, Aug. 1, 2018, pp. 53-62, vol. 99, Publisher: Computers in Biology and Medicine.

Sameer Mehta, Non-Final Office Action issued in U.S. Appl. No. 16/654,970, filed Dec. 17, 2019.

Sameer Mehta, Non-Final Office Action issued in related U.S. Appl. No. 16/854,970, filed Jul. 8, 2020.

Sameer Mehta, Non-Final Office Action issued in U.S. Appl. No. 16/654,854, filed May 4, 2021.

Sameer Mehta, Non-Final Office Action issued in U.S. Appl. No. 16/654,970, filed Jun. 9, 2021.

* cited by examiner

PATIENT-TRIGGERED SYSTEM FOR CARDIAC EMERGENCIES

CLAIM OF PRIORITY

The present application claims priority under 35 U.S.C. § 119 to a U.S. provisional patent application having Ser. No. 63/324,446 and having a filing date of Mar. 28, 2022, which is explicitly incorporated herein by reference in its entirety.

BACKGROUND OF THE INVENTION

Field of the Invention

The present invention is directed to patient-triggered system for cardiac emergencies. More specifically, the present invention relates to a central processor configured to transmit a multi-alert signal in the event of a cardiac emergency.

Description of the Related Art

Heart attacks, in both men and women, constitute one of the most prominent causes of death for mankind, accounting for more than approximately seven (7) million deaths per year. Nearly every forty (40) seconds, someone in the United States will have a heart attack. The estimated annual incidence of heart attacks in the United States is approximately 805,000, with this figure representing 605,000 new heart attacks and 200,000 recurrent heart attacks. The estimated average annual direct and indirect cost of heart disease is $230 billion in the United States alone. Because of its colossal impact on morbidity, mortality, and cost, treating and preventing heart attacks is a major priority in healthcare systems across the globe.

Strides have been made in the urgent management of patients with a heart attack. The pathology of a heart attack includes an occlusion, often by a fresh blood clot, that impairs flow from the coronary artery to the heart muscle. There is urgency required in unclogging an occluded coronary artery, as with every passing minute, the heart muscle is permanently damaged.

Heart attacks are of two (2) types, based upon the severity and upon the method of diagnosis by an electrocardiogram (ECG). These two types are ST-elevation Myocardial Infarction or "STEMI," and Non ST-elevation Myocardial Infarction or "NSTEMI." By and large, it is STEMI that requires more urgent revascularization of the occluded coronary artery. Treatment includes urgent angioplasty to unclog occluded coronary arteries. In the majority of cases, a diagnosis of STEMI is made with the ECG that detects elevation of a portion of the ECG waveform.

Globally, a majority of heart attack patients are now treated with Primary PCI, which has emerged as the most effective form of aborting a heart attack. It is performed in a designated area of the hospital, known as the Cardiovascular Laboratory (CVL). This procedure requires a trained team of medical personnel, as well as specific equipment. However, this treatment and others are not available to most patients in a timely fashion. This is a result of, for example, challenging logistics. Hospitals must organize heart attack teams that urgently respond to the situation and take the patient to the CVL where a trained cardiologist performs the Primary PCI.

With this methodology, every hospital in the country has been designated as either a Primary PCI hospital or a Non-PCI hospital, with PCI hospitals performing so-called STEMI care. A benchmark for measuring STEMI care is the metric of "door-to-balloon" (d2b) time, which measures the time it takes from the moment the patient enters the door of the hospital until the culprit vessel that is causing the heart attack has been opened with angioplasty. The d2b metric measures the performance of STEMI systems.

Numerous strategies have been developed to reduce d2b times, such as the backward integration of STEMI care and decision-making. Rather than beginning the care of the heart attack patient at the emergency room of a hospital, several important decisions have been moved back to the team that provides care for such patients, like emergency medical services. Strategies have also been developed to activate the heart attack management process before the patient reaches the hospital itself, such as the performance and diagnosis of the ECG in the ambulance itself. The challenge is the reliable and accurate interpretation of the ECG in the ambulance.

The challenges associated with accurate interpretation of the ECG in the ambulance are many, such as false positives generated from software designed to read ECGs. ECGs may also be remotely provided via fax, for example, to a cardiologist or other medical professional, but such strategies are time-consuming, not instantaneous, and can be unreliable.

A significant reducer of d2b times is the bypass of the emergency department (known as "ED bypass") which involves a heart attack patient bypassing the traditional stop in the emergency department of a hospital. ED bypass is considered only for patients transported by emergency medical services, and not for those that self-transport to the hospital. Despite its potential impact on d2b times, ED bypass is largely not yet possible as the coordination between medical teams can be extremely difficult. For an ED bypass to function, the CVL team needs to be available and ready as the ambulance approaches the hospital.

The STEMI system has much room for improvement, and there are large gaps to be filled. Despite the strides made with the d2b metric, there is a missing link that represents gains that are bigger than d2b, namely, the symptom-to-balloon (s2b) time, which emphasizes the time a patient experiences symptoms until the angioplasty is performed. This is because the s2b time stresses the damage done to the heart muscle and treatment of the heart attack. There are numerous delays in a patient reaching the hospital, which are unaccounted for in d2b time. Therefore, despite d2b gains, the challenge of s2b has not been addressed.

Further, traditional systems and methods of providing a patient medical attention during a cardiac event are far too time-consuming, inefficient, and are not streamlined. Such systems and methods generally include the patient or another person contacting an emergency call center such as 911, and 911 thereafter contacts emergency medical services for an ambulance dispatch. Upon calling 911, the patient must provide information such as their name, location, and symptoms. However, often the patient is unable to communicate, frazzled, confused, or may be nearly unconscious. When an ambulance arrives, an ECG may not be taken, and the determination of which facility to which to transport the patient is made. A patient that requires STEMI care may be transported to a non-PCI facility, which wastes time in the treatment process and results in further damage to the heart muscle. Further, once the patient has arrived at the hospital, the patient typically must go through the traditional stop at the emergency department for initial evaluation and usually an ECG. The ECG is then evaluated by a cardiologist and a treatment plan is developed. Additional time is required to ensure that a CVL team is assembled, a surgery room is prepared, and all equipment is ready for use. All the while, precious minutes are lost and further damage to the heart muscle results. There is a lack of coordination in current systems that prevent efficient treatment of the patient, resulting in extremely high s2b times.

Accordingly, in view of the foregoing disadvantages of present systems and related methods, there is a need for a patient-triggered system for cardiac emergencies which reduces s2b time and facilitates a more efficient, streamlined, and less time-consuming cardiac patient treatment process.

SUMMARY OF THE INVENTION

In view of the foregoing disadvantages that come with current systems, the present invention is directed to patient-triggered system for cardiac emergencies. More specifically, the present invention relates to a central processor configured to transmit a multi-alert signal in the event of a cardiac emergency.

The system comprises a central processor and a multi-alert signal, wherein the central processor is configured to transmit the multi-alert signal. The system further comprises at least one bottleneck department, with the multi-alert signal configured to bypass the at least one bottleneck department. Additionally, the system comprises a patient assembly configured to communicate with the central processor. The system further comprises a hospital assembly, a highest authority assembly, and an emergency services assembly, with the highest authority assembly configured to communicate with the hospital assembly and the emergency services assembly.

The patient assembly comprises a patient device, a patient initiation mechanism, a patient signal, and at least one patient detail. The patient device is configured to house the patient initiation mechanism, and the patient initiation mechanism is configured to transmit the patient signal to the central processor. The central processor is configured to receive the patient signal.

In the preferred embodiment, the patient initiation mechanism is further configured to receive the at least one patient detail and transmit the at least one patient detail to the central processor. The central processor is further configured to receive and store the at least one patient detail. Preferably, the at least one patient detail comprises a baseline electrocardiogram.

Further, it is preferred that the central processor is configured to transmit the multi-alert signal upon receipt of the patient signal. In the preferred embodiment, the central processor's receipt of the patient signal acts as a trigger that generates the multi-alert signal. It is also preferred that the patient signal comprises a patient location, with the central processor configured to transmit the patient location via the multi-alert signal.

The emergency services assembly comprises a dispatch device, a dispatch signal, a responder device, and a responder signal. The dispatch device is configured to receive the multi-alert signal and transmit the dispatch signal, and the responder device is configured to receive the dispatch signal and transmit a responder signal.

The highest authority assembly comprises a highest authority device configured to receive the multi-alert signal and the responder signal. The highest authority assembly further comprises a highest authority signal, and the highest authority device is configured to transmit the highest authority signal. Lastly, the responder device is further configured to receive the highest authority signal.

In the preferred embodiment, the multi-alert signal is further configured to transmit the at least one patient detail to the highest authority device. It is preferred that such transmission of the at least one patient detail to the highest authority device is instantaneous upon the central processor's receipt of the patient signal.

Additionally, the emergency services assembly preferably further comprises an electrocardiogram machine, an electrocardiogram signal, and at least one new medical detail. The electrocardiogram machine is configured to generate the at least one new medical detail, and is further configured to transmit the electrocardiogram signal. It is preferred that the at least one new medical detail comprise a symptomatic electrocardiogram. Moreover, in the preferred embodiment, the at least one new medical detail is configured to be transmitted to the highest authority device via the electrocardiogram signal, and the highest authority device is further configured to receive the electrocardiogram signal.

In another embodiment, the responder device is configured to receive the at least one new medical detail via the electrocardiogram signal and is further configured to transmit the at least one new medical detail to the highest authority device via the responder signal.

It is preferred that the highest authority assembly further comprise a highest authority tracking element, which is configured to transmit the multi-alert signal to the highest authority device. In simpler terms, the highest authority tracking element is preferably configured to track the appropriate highest authority device to which the multi-alert signal should be transmitted. Further, it is preferred that the patient signal comprises a patient location, with the central processor being further configured to transmit the patient location to the highest authority tracking element. Preferably, the highest authority tracking element is configured to analyze the patient location to further assist in the determination of the appropriate highest authority tracking device to which the multi-alert signal should be transmitted.

The hospital assembly comprises a hospital device and a hospital signal, with the hospital device configured to transmit the hospital signal and receive the multi-alert signal as well as receive the highest authority signal. The central processor is further configured to transmit the multi-alert signal to the hospital device. It is preferred that the highest authority device is further configured to receive the hospital signal. Moreover, the hospital device is further configured to receive the responder signal the responder device is similarly further configured to receive the hospital signal in the preferred embodiment.

The hospital assembly preferably further comprises a hospital coordinator device configured to receive the multi-alert signal, with the central processor being further configured to transmit the multi-alert signal to the hospital coordinator device. The hospital assembly further comprises a hospital coordinator signal, and the hospital coordinator device is configured to transmit the hospital coordinator signal in this embodiment. Preferably, the hospital coordinator device is further configured to receive the highest authority signal, and the highest authority device is similarly further configured to receive the hospital coordinator signal.

Finally, the system may further comprise a primary doctor device configured to receive the multi-alert signal, with the central processor being further configured to transmit the multi-alert signal to the primary doctor device. Additionally, the system may further comprise at least one emergency contact device configured to receive the multi-alert signal, with the central processor being further configured to transmit the multi-alert signal to the at least one emergency contact device.

These and other objects, features and advantages of the present invention will become clearer when the drawings as well as the detailed description are taken into consideration.

BRIEF DESCRIPTION OF THE DRAWINGS

For a fuller understanding of the nature of the present invention, reference should be had to the following detailed description taken in connection with the accompanying drawings in which.

Like reference numerals refer to like parts throughout the several views of the drawings.

DETAILED DESCRIPTION OF THE PREFERRED EMBODIMENT

Figure 1:
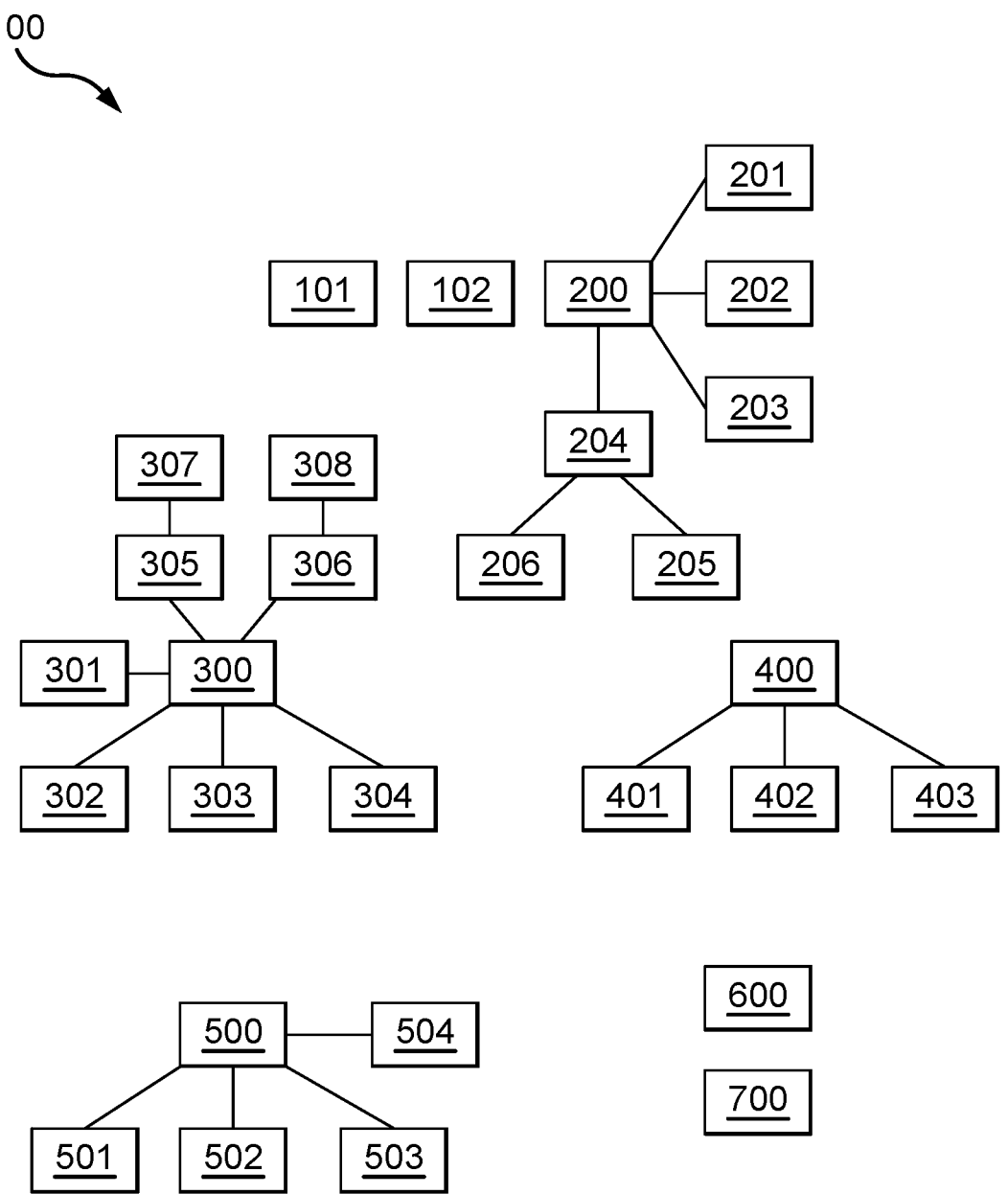
FIG. 1 is a schematic representation of the patient-triggered system for cardiac emergencies.
Figure 2:
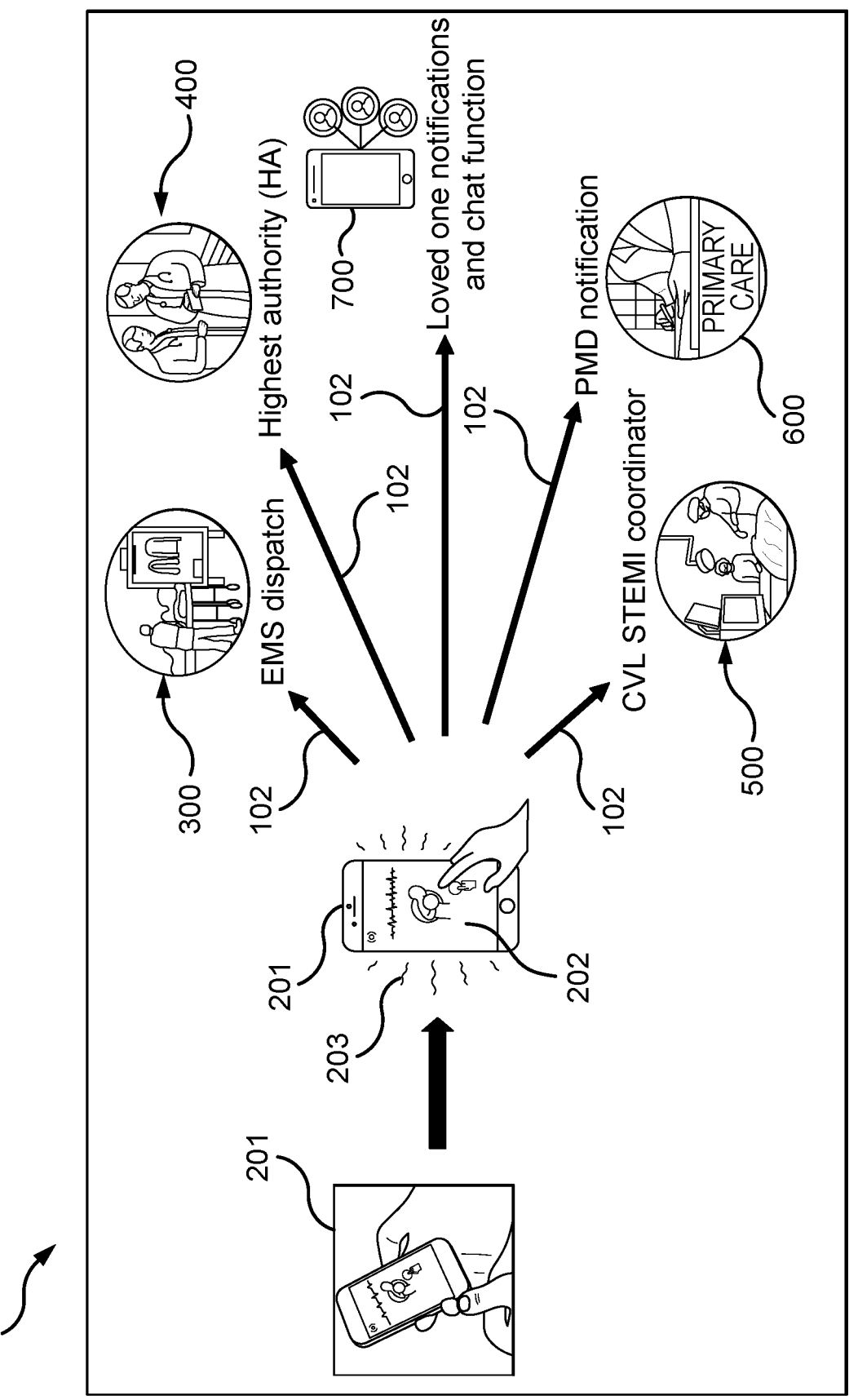
FIG. 2 is a schematic representation of the patient-triggered system for cardiac emergencies.

The system 100 comprises a central processor 101 and a multi-alert signal 102, wherein the central processor 101 is configured to transmit the multi-alert signal 102. The central processor 101 may be any type of processor and/or computer. As discussed in detail below, the central processor 101 is configured to transmit the multi-alert signal 102 to one or more devices. The multi-alert signal 102 is a notification or alert that is preferably transmitted to at least three (3) devices (namely, a highest authority device 401, a hospital device 501, and a dispatch device 301, as explained fully below). However, the multi-alert signal 102 may be transmitted to any number of devices, including just one (1). The multi-alert signal 102 is configured to provide information to the device(s) to which the multi-alert signal 102 was transmitted. If transmitted to more than one device, such information may differ between devices, but may also be identical or have just some overlapping information. Such information may also be displayed on the device(s).

The system 100 further comprises at least one bottleneck department, with the multi-alert signal 102 configured to bypass the at least one bottleneck department. The at least one bottleneck department may be any type of department (s), such as a 911 call center (which may consume time by speaking with a patient, connecting to an ambulance, directing the ambulance, etc.) and/or a hospital department(s), such as an emergency room (which may consume time by performing an on-site electrocardiogram, locating a doctor to diagnose a heart attack on-site before treatment is provided, etc.). In general, the at least one bottleneck department may be any type of department(s) which contribute(s) to the symptom-to-balloon (s2b) time in a cardiac emergency, or at least does not contribute to the decrease of s2b time. As will become clearer from the below, the multi-alert signal 102 enables the system 100 to bypass the at least one bottleneck department by expediting and streamlining tasks normally performed by the at least one bottleneck department. As just one example, the multi-alert signal may enable the bypass of the 911 call center by instantly transmitting the location and symptom of the patient to an ambulance dispatch center.

Additionally, the system 100 comprises a patient assembly 200 configured to communicate with the central processor 101. The system 100 further comprises a hospital assembly 500, a highest authority assembly 400, and an emergency services assembly 300, with the highest authority assembly 400 configured to communicate with the hospital assembly 500 and the emergency services assembly 300. Each of the foregoing assemblies are discussed in detail below, in turn.

The patient assembly 200 comprises a patient device 201, a patient initiation mechanism 202, a patient signal 203, and at least one patient detail 204.

The patient device 201 is preferably a cellular telephone, but may be any other device such as a tablet, smartwatch, laptop, computer, or another wearable device. The user of the patient device 201 is a person who anticipates the need for emergency medical treatment (known as "the patient"). The patient device 201 is configured to house the patient initiation mechanism 202. For example, the patient initiation mechanism 202 may be an application installed on the patient device 201, but it may be any other mechanism, including a physical mechanism rather than a digital one, such as a physical button that is pushed by the patient. The patient signal 203 may be any type of signal, such as cellular or wireless signal.

The patient initiation mechanism 202 is configured to transmit the patient signal 203 to the central processor 101, and the central processor 101 is configured to receive the patient signal 203. Further, it is preferred that the central processor 101 is configured to transmit the multi-alert signal 102 upon receipt of the patient signal 203. In the preferred embodiment, the central processor's 101 receipt of the patient signal 203 acts as a trigger that generates the multi-alert signal 102.

More specifically, the central processor 101 is ideally configured to understand the patient signal 203 as an indication that the patient needs emergency assistance. Accordingly, in the preferred embodiment, the central processor's 101 receipt of the patient signal 203 is a trigger for the central processor 101 to transmit the multi-alert signal 102. This transmission of the multi-alert signal 102 by the central processor 101 is preferably instantaneous following the receipt of the patient signal 103, though it may not be instantaneous in alternative embodiments. For example, the system 100 may delay or provide the patient an option to delay the transmission of the multi-alert signal 101, perhaps to account for instances wherein the patient signal 203 may have been transmitted in error.

The patient initiation mechanism 202 may also be configured to transmit the patient signal 203 to the central processor 101 automatically, such as upon detecting an abnormal heart rhythm or upon receipt of information from another system or a related system regarding an abnormal symptom(s), or when explicitly triggered to do by the patient. This transmission of the patient signal 203 to the central processor 101 may be catalyzed or initiated via an additional feature of the patient initiation mechanism 202 in some embodiments. Returning to the illustration wherein the patient initiation mechanism 202 is an application installed on the patient device 201 as an example, the patient initiation mechanism 202 may be configured to transmit the patient signal 203 upon the engagement of a such an additional feature, like a digital button.

In the preferred embodiment of the system 100, the patient initiation mechanism 202 is further configured to receive the at least one patient detail 204 and transmit the at least one patient detail 204 to the central processor 101. The central processor 101 is further configured to receive and store the at least one patient detail 204. Preferably, the at least one patient detail 204 comprises a baseline electrocardiogram 205, but the at least one patient detail 204 may comprise any information, such as name, age, gender, GPS location, medical history, allergies, current medications, medical provider information, previous medical imaging files, and/or log-in credentials associated with the patient initiation mechanism 202, etc., of the patient.

For a simple illustration of one embodiment, the patient may upload the at least one patient detail 204 (such as the baseline electrocardiogram 205) into the patient initiation mechanism 202 (which may be an application installed on the patient device 201). Once the at least one patient detail 204 is uploaded to the patient initiation mechanism 202, the at least one patient detail 204 is transmitted to the central processor 101, which is configured to receive and store the at least one patient detail 204. The at least one patient detail 204 is stored at the ready in the central processor 101, making the at least one patient detail 204 available on demand. As described more fully below, the at least one patient detail 204 thereby becomes available for transmission to other devices of the system 100 via the multi-alert signal 102, which can contribute to the decrease of s2b time in the event of a cardiac emergency.

It is also preferred that the patient signal 203 comprises a patient location 206, with the central processor 101 configured to transmit the patient location 206 via the multi-alert signal 102. The patient location 206 comprises information about where the patient is located when the patient signal 203 was transmitted to the central processor 101. The patient location 206 may be determined via GPS tracking that is, for example, a feature of the patient device 201 or the patient initiation mechanism 202. In another embodiment, the patient location 206 may be manually, verbally, automatically, or otherwise provided to or obtained by the system 100.

The emergency services assembly 300 comprises a dispatch device 301, a dispatch signal 302, a responder device 303, and a responder signal 304. The dispatch device 301 is configured to receive the multi-alert signal 102 and transmit the dispatch signal 302, and the responder device 303 is configured to receive the dispatch signal 302 and transmit a responder signal 304. The dispatch device 301 and the responder device 303 may each be any device, such as a telephone or radio. Further, the dispatch signal 302 and the responder signal 304 may be any type of signal, such as a cellular signal or radio wave. The transmission of the multi-alert signal 102 to the dispatch device 301 enables the bypass of at least one bottleneck department, such as a 911 call center, and thereby reduces the s2b time in a given cardiac emergency.

The highest authority assembly 400 comprises a highest authority device 401 configured to receive the multi-alert signal 102 and the responder signal 304. The highest authority device 401 may be any device, such as a telephone, tablet, laptop, computer, smartwatch, or another wearable device. The highest authority assembly 400 further comprises a highest authority signal 402, and the highest authority device 401 is configured to transmit the highest authority signal 402. The highest authority signal 402 may be any type of signal, such as cellular signal or wireless signal. Lastly, the responder device 303 is further configured to receive the highest authority signal 402.

The multi-alert signal 102 transmitted to the highest authority device 401 alerts regarding the instant emergency, permitting additional time for treatment preparation. The foregoing also demonstrates the system's facilitation of communication between the user of the responder device 303 (a person responding to the patient's emergency, such as an EMT in an ambulance, known as the "responder") and the user of the highest authority device 401 (a medical professional with expertise in cardiology, such as an interventional cardiologist, known as the "highest authority" in cardiac emergencies). In this illustrative scenario, the highest authority is able to directly communicate with the responder, meaning the at least one bottleneck department may include at least the emergency room or emergency department at a hospital, which is bypassed due to this communication between the responder and the highest authority. This also reduces the s2b time.

In the preferred embodiment, the multi-alert signal 102 is further configured to transmit the at least one patient detail 204 to the highest authority device 401. Again, the at least one patient detail 204 may comprise a baseline electrocardiogram 205, and/or other information. It is preferred that such transmission of the at least one patient detail 204 to the highest authority device 401 is instantaneous upon the central processor's 101 receipt of the patient signal 203. The transmission of the at least one patient detail 204 to the highest authority device 401 enables the highest authority to review the baseline electrocardiogram 205 and/or other information provided via the at least one patient detail 204 in preparation for treatment, including in preparation for the comparison of the baseline electrocardiogram 205 to further medical imaging or for the consideration of additional medical information.

In addition, the emergency services assembly 300 preferably further comprises an electrocardiogram machine 305, an electrocardiogram signal 306, and at least one new medical detail 307. The electrocardiogram machine 305 may be any machine capable of taking an electrocardiogram and/or other medical imaging, and may also be another type of machine capable of collecting any medical information. Further, the electrocardiogram machine 305 may be in the possession of the responder or the patient. The electrocardiogram signal 306 may be any type of signal, such as cellular signal, Bluetooth signal or wireless signal.

Importantly, the electrocardiogram machine 305 is configured to generate the at least one new medical detail 307 and transmit the electrocardiogram signal 306. It is preferred that the at least one new medical detail 307 comprise a symptomatic electrocardiogram 308, but the at least one new medical detail 307 may comprise other medical information and/or imaging in alternative embodiments. The symptomatic electrocardiogram 308 is one taken while the patient is experiencing symptoms of a heart attack, and may be taken before or after the responder has arrived at the patient location 206. Nonetheless, the at least one new medical detail 307 may comprise other information, such as a blood pressure reading or a list of symptoms, as noted above.

Moreover, in the preferred embodiment, the at least one new medical detail 307 is configured to be transmitted to the highest authority device 401 via the electrocardiogram signal 306, and the highest authority device 401 is further configured to receive the electrocardiogram signal 306. To illustrate, in the scenario wherein the at least one new medical detail 307 is the symptomatic electrocardiogram 308, the at least one bottleneck is bypassed as the highest authority may compare the baseline electrocardiogram 205 to the symptomatic electrocardiogram 308. In this scenario, the at least one bottleneck includes, at minimum, the emergency room or emergency department at the hospital to which the patient is transported. This is because the comparison of the symptomatic electrocardiogram 308 to the baseline electrocardiogram 205 may be performed by the highest authority before the patient reaches the hospital, facilitating a much quicker diagnosis and determination of a treatment plan.

In another embodiment, the responder device 304 is configured to receive the at least one new medical detail 307 via the electrocardiogram signal 306 and is further configured to transmit the at least one new medical 307 detail to the highest authority device 401 via the responder signal 304. Here, the responder may, for example, receive the at least one new medical detail 307 to the responder device 303 via the electrocardiogram signal 306 and then manually transmit the at least one new medical detail 307 from the responder device 303 to the highest authority device 401. The foregoing facilitates the bypass of the at least one bottleneck department as well.

Next, it is preferred that the highest authority assembly 400 further comprise a highest authority tracking element 403, which is configured to transmit the multi-alert signal 102 to the highest authority device 401. The highest authority tracking element 403 may be any system or method of tracking on-call or available personnel, such as a GPS tracker or a database of on-call personnel at a given hospital facility perhaps with an algorithm to employ the same. In simpler terms, the highest authority tracking element 403 is preferably configured to track the appropriate highest authority device 401 to which the multi-alert signal 102 should be transmitted.

Further, it is preferred that the patient signal 203 comprises a patient location 206, with the central processor 101 being further configured to transmit the patient location 206 to the highest authority tracking element 403. Preferably, the highest authority tracking element 403 is configured to analyze the patient location 206 to further assist in the determination of the appropriate highest authority device 401 to which the multi-alert signal should be transmitted. To illustrate, the highest authority tracking element 403 may use the patient location 206 to determine which hospital is closest in proximity to the patient location 206 when the patient signal 203 was transmitted to the central processor 101, and also determine the highest authority on-call when the patient signal 203 was transmitted. Thus, the highest authority tracking element 403 preferably directs the multi-alert signal 102 to the highest authority device 401 belonging to the highest authority that is on-call at the time of the emergency at the hospital nearest the patient location 206. Preferably, the highest authority tracking element 403 pairs the multi-alert signal 102 with the highest authority device 401 that is appropriate at the time of the emergency, and transmits the multi-alert signal 102 to such highest authority device 401.

Next, the hospital assembly 500 comprises a hospital device 501 and a hospital signal 502, with the hospital device 501 configured to transmit the hospital signal 502 and receive the multi-alert signal 102 as well as receive the highest authority signal 402. The central processor 101 is further configured to transmit the multi-alert signal 102 to the hospital device 501.

It is preferred that the highest authority device 401 is further configured to receive the hospital signal 501. The foregoing facilitates communication between the highest authority and the user of the hospital device (known as the "hospital worker"), which reduces the s2b time because, for example, the highest authority may provide instructions to the hospital worker regarding treatment preparation.

Moreover, the hospital device 501 is further configured to receive the responder signal 304, and the responder device 303 is similarly further configured to receive the hospital signal 502 in the preferred embodiment. This facilitation of communication between the hospital worker and the responder reduces s2b time by, for example, efficiently assisting with the coordination of logistics between the ambulance and the hospital.

The hospital assembly 500 preferably further comprises a hospital coordinator device 503 configured to receive the multi-alert signal 102, with the central processor 101 being further configured to transmit the multi-alert signal 102 to the hospital coordinator device 503. The hospital coordinator device 503 may be any device, such as a telephone, tablet, computer, laptop, smartwatch, pager, or radio. The multi-alert signal 102 transmitted to the hospital coordinator device 503 alerts the user of the hospital coordinator device 503 (known as the "hospital coordinator," who is preferably a STEMI coordinator at the hospital to which the patient will be transported) to the emergency and the need to prepare for treatment.

The hospital assembly further comprises a hospital coordinator signal 504, and the hospital coordinator device 503 is configured to transmit the hospital coordinator signal 504 in this embodiment. The hospital coordinator signal 504 may be any type of signal, such as cellular signal or wireless signal. The hospital assembly 500 may further comprise a hospital coordinator tracking element, similar to that of the highest authority tracking element 403, but used to track the on-call hospital coordinator at a given hospital facility instead of the on-call highest authority.

Preferably, the hospital coordinator device 503 is further configured to receive the highest authority signal 402, and the highest authority device 401 is similarly further configured to receive the hospital coordinator signal 504. The multi-alert signal 102 transmitted to the hospital coordinator device 503, as well as the communication facilitated between the hospital coordinator device 503 and the highest authority device 401, reduce s2b times by, for example, enabling the hospital coordinator to mobilize a treatment team, prepare the treatment room, and prepare equipment for treatment in advance of the patient's arrival to the hospital.

Next, the system 100 may further comprise a primary doctor device 600 configured to receive the multi-alert signal 102, with the central processor 101 being further configured to transmit the multi-alert signal 101 to the primary doctor device 600. The primary doctor device 600 may be a telephone, tablet, smartwatch, computer, laptop, or any other device. The multi-alert signal 102 notifies the user of the primary doctor device 600 (known as the "primary doctor") that the patient is experiencing an emergency. This gives the primary doctor an opportunity to reach the hospital at which treatment will be provided to, for example, assist with treatment and/or provide insight as to the patient's medical history, ultimately facilitating more informed treatment.

Finally, the system 100 may further comprise at least one emergency contact device 700 configured to receive the multi-alert signal 102, with the central processor 101 being further configured to transmit the multi-alert signal 102 to the at least one emergency contact device 700. The at least one emergency contact device 700 may be a telephone, tablet, smartwatch, computer, laptop, or any other device. In this embodiment, the multi-alert signal 102 may provide information to the at least one emergency contact device 700, such as the patient location 206 and/or other information regarding the patient's status, such as the hospital to which the patient is being transported. The patient initiation mechanism 202 may further include a chat function that is configured to facilitate communication between the patient device 201 and the at least one emergency contact device 700. The chat function may comprise a two-way messaging function, a video communication function, and/or additional communication functions.

Since many modifications, variations and changes in detail can be made to the described embodiments of the invention, it is intended that all matters in the foregoing description and shown in the accompanying drawings be interpreted as illustrative and not in a limiting sense. Thus, the scope of the invention should be determined by the appended claims and their legal equivalents.

What is claimed is:

1. A patient-triggered system for cardiac emergencies, comprising:
    a central processor;
    a multi-alert signal;
    said central processor configured to transmit said multi-alert signal;
    at least one bottleneck department;
    said multi-alert signal configured to bypass the at least one bottleneck department;
    a patient assembly;
    said patient assembly configured to communicate with said central processor;
    said patient assembly comprising:
    a patient device;
    a patient initiation mechanism;
    said patient device configured to house said patient initiation mechanism;
    a patient signal;
    said patient initiation mechanism configured to initiate transfer of said patient signal to said central processor upon actuation of said patient initiation mechanism;
    said central processor being configured to receive said patient signal; and
    at least one patient detail;
    an emergency services assembly;
    said emergency services assembly comprising:
        a dispatch device,
        a dispatch signal,
        a responder device, and
        a responder signal,
        said dispatch device being configured to receive said multi-alert signal and transmit said dispatch signal, and
        said responder device being configured to receive said dispatch signal and transmit said responder signal;
    a hospital assembly; and
    a highest authority assembly; and
    said highest authority assembly comprising:
        a highest authority device configured to receive said multi-alert signal and said responder signal, and
        a highest authority signal, and
        said highest authority device configured to transmit said highest authority signal; and
    said responder device being further configured to receive said highest authority signal;
    and
    said highest authority assembly configured to communicate with said hospital assembly and said emergency services assembly.

2. The system of claim 1, wherein said patient initiation mechanism is further configured to initiate receipt of said at least one patient detail and initiate transfer of said at least one patient detail to said central processor, upon actuation of said patient initiation mechanism; said central processor being further configured to receive and store said at least one patient detail.

3. The system of claim 2, wherein said at least one patient detail comprises a baseline electrocardiogram.

4. The system of claim 1, wherein said central processor is configured to transmit said multi-alert signal upon receipt of said patient signal.

5. The system of claim 1, wherein said patient signal comprises a patient location; said central processor configured to transmit said patient location via said multi-alert signal.

6. The system of claim 1, wherein said multi-alert signal is further configured to transmit said at least one patient detail to said highest authority device.

7. The system of claim 1, wherein said emergency services assembly further comprises an electrocardiogram machine, an electrocardiogram signal, and at least one new medical detail; said electrocardiogram machine being configured to generate said at least one new medical detail and further configured to transmit said electrocardiogram signal.

8. The system of claim 7, wherein said at least one new medical detail comprises a symptomatic electrocardiogram.

9. The system of claim 7, wherein said at least one new medical detail is configured to be transmitted to said highest authority device via said electrocardiogram signal; said highest authority device being configured to receive said electrocardiogram signal.

10. The system of claim 7, wherein said responder device is configured to receive said at least one new medical detail via said electrocardiogram signal and is further figured to transmit said at least one new medical detail to said highest authority device via said responder signal.

11. The system of claim 1, wherein said highest authority assembly further comprises a highest authority tracking element; said highest authority tracking element configured to transmit said multi-alert signal to said highest authority device.

12. The system of claim 11, wherein said patient signal comprises a patient location; said central processor being further configured to transmit said patient location to said highest authority tracking element.

13. The system of claim 1, wherein said hospital assembly comprises a hospital device and a hospital signal; said hospital device configured to transmit said hospital signal, receive said multi-alert signal, and receive said highest authority signal; said central processor being further configured to transmit said multi-alert signal to said hospital device.

14. The system of claim 13, wherein said highest authority device is further configured to receive said hospital signal.

15. The system of claim 13, wherein said hospital device is further configured to receive said responder signal and said responder device is further configured to receive said hospital signal.

16. The system of claim 13, wherein said hospital assembly further comprises a hospital coordinator device configured to receive said multi-alert signal; said central processor being further configured to transmit said multi-alert signal to said hospital coordinator device.

17. The system of claim 16, wherein said hospital assembly further comprises a hospital coordinator signal; said hospital coordinator device configured to transmit said hospital coordinator signal.

18. The system of claim 17, wherein said hospital coordinator device is further configured to receive said highest authority signal and said highest authority device is further configured to receive said hospital coordinator signal.

19. The system of claim 1, further comprising a primary doctor device configured to receive said multi-alert signal;

said central processor being further configured to transmit said multi-alert signal to said primary doctor device.

20. The system of claim 1, further comprising at least one emergency contact device configured to receive said multi-alert signal; said central processor being further configured to transmit said multi-alert signal to said at least one emergency contact device.

21. A patient-triggered system for cardiac emergencies, comprising:

a central processor;

a multi-alert signal;

said central processor configured to transmit said multi-alert signal;

at least one bottleneck department;

said multi-alert signal configured to bypass the at least one bottleneck department;

a patient assembly comprising a patient device, a patient initiation mechanism, at least one patient detail, and a patient signal;

said patient device configured to house said patient initiation mechanism;

said patient initiation mechanism configured to initiate receipt of said at least one patient detail and configured to initiate transfer of said at least one patient detail to said central processor, upon actuation of said patient initiation mechanism;

said central processor configured to receive and store said at least one patient detail;

said patient initiation mechanism configured to transmit said patient signal to said central processor, said central processor being configured to receive said patient signal;

an emergency services assembly comprising a dispatch center device, a dispatch signal, a responder device, and a responder signal;

said dispatch center device configured to receive said multi-alert signal and transmit a dispatch signal;

said responder device configured to receive said dispatch signal and transmit a responder signal;

a hospital assembly comprising a hospital device and a hospital signal;

said hospital device configured to transmit said hospital signal;

said hospital device configured to receive said multi-alert signal and said responder signal;

said responder device further configured to receive said hospital signal;

a highest authority assembly comprising a highest authority device and a highest authority signal;

said highest authority device configured to receive said multi-alert signal;

said highest authority device configured to receive said responder signal and said hospital signal; and said responder device and said hospital device each configured to receive said highest authority signal.

* * * * *